(12) United States Patent
Glavicic et al.

(10) Patent No.: US 7,978,821 B1
(45) Date of Patent: Jul. 12, 2011

(54) LAUE CRYSTALLOGRAPHIC ORIENTATION MAPPING SYSTEM

(75) Inventors: Michael G. Glavicic, Indianapolis, IN (US); Pamela A. Kobryn, Westerville, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 12/370,987

(22) Filed: Feb. 13, 2009

Related U.S. Application Data

(60) Provisional application No. 61/070,616, filed on Feb. 15, 2008.

(51) Int. Cl.
*G01N 23/203* (2006.01)

(52) U.S. Cl. .................................................. 378/76

(58) Field of Classification Search .............. 378/71, 378/72, 73, 74, 76, 79, 80, 81
See application file for complete search history.

(56) References Cited

U.S. PATENT DOCUMENTS

| | | | |
|---|---|---|---|
| 2,967,240 A * | 1/1961 | Koch | 378/78 |
| 4,217,493 A * | 8/1980 | Li et al. | 378/73 |
| 4,247,771 A * | 1/1981 | Frevel | 378/75 |
| 4,862,488 A | 8/1989 | Schiller | |
| 5,629,524 A | 5/1997 | Stettner et al. | |
| 6,057,552 A | 5/2000 | Stettner et al. | |
| 6,173,036 B1 * | 1/2001 | Hossain et al. | 378/45 |
| 6,198,796 B1 | 3/2001 | Yokoyama et al. | |
| 7,139,365 B1 * | 11/2006 | Janik | 378/70 |
| 2006/0176998 A1 * | 8/2006 | Korsunsky | 378/71 |

OTHER PUBLICATIONS

M.G. Glavicic et al., "A Method to Determine the Orientation of the High-Temperature Beta Phase from Measured EBSD Data for the Low-Temperature Alpha Phase in Ti-6Al-4V", Materials Science and Engineering A346 (2003), pp. 50-S9.
U. Lienert et al., "Three-Dimensional High-Energy Diffraction Microscopy of Polycrystalline Bulk Materials", SRMS-S Conference, Chicago IL, Jul. 30-Aug. 2, 2006, p. 201.

* cited by examiner

*Primary Examiner* — Chih-Cheng G Kao
(74) *Attorney, Agent, or Firm* — AFMCLO/JAZ; Jeffrey R. Moore

(57) ABSTRACT

A device for measuring crystal orientation with an x-ray source using the Laue method and includes an apparatus for mapping a polycrystalline surface having a grain orientation. The apparatus including an x-ray source creating an x-ray beam, the beam having polychromatic photons, the beam collimated to a point on the polycrystalline surface. A two-dimensional x-ray detector with an aperture, the x-ray beam passing through the aperture, the detector detecting and collecting polychromatic photons diffracted from the polycrystalline surface and onto the detector. A means for moving the polycrystalline surface with respect to the x-ray source to collect a plurality of diffracted x-rays which define a Laue pattern. A data processing means to collect Laue patterns of the polycrystalline surface based upon the plurality of diffracted x-rays, the Laue patterns identifying a plurality of crystallographic orientations and a plurality of grain surface areas on the polycrystalline surface.

9 Claims, 3 Drawing Sheets

Beta Phase

Alpha Phase

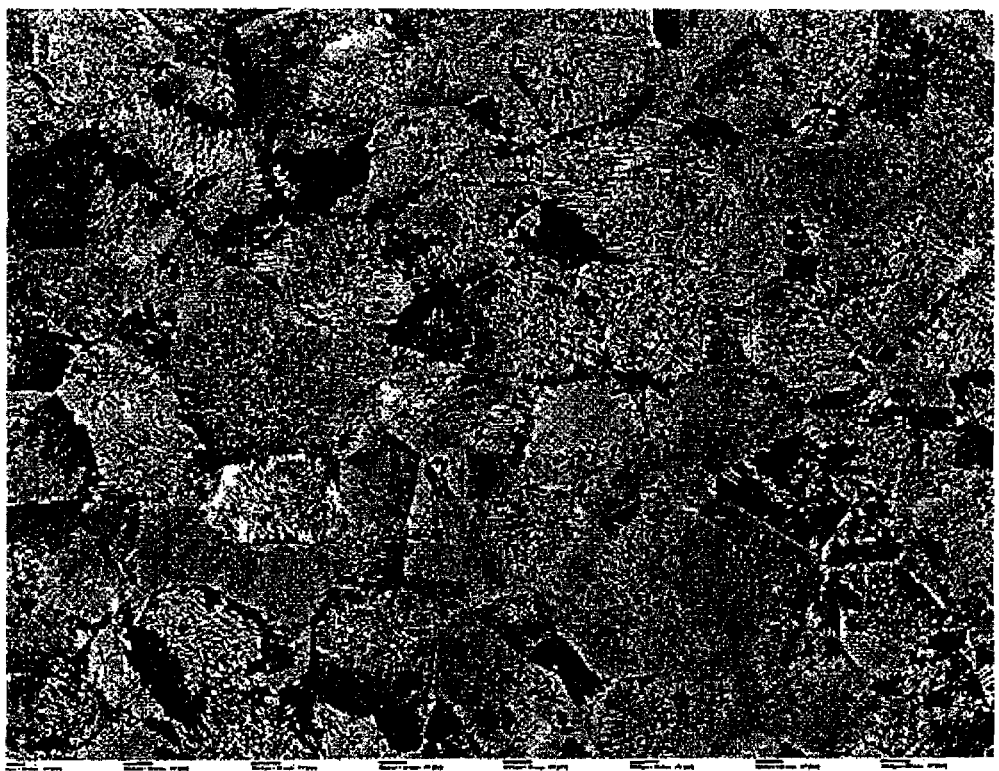
Alpha  Fig. 3a
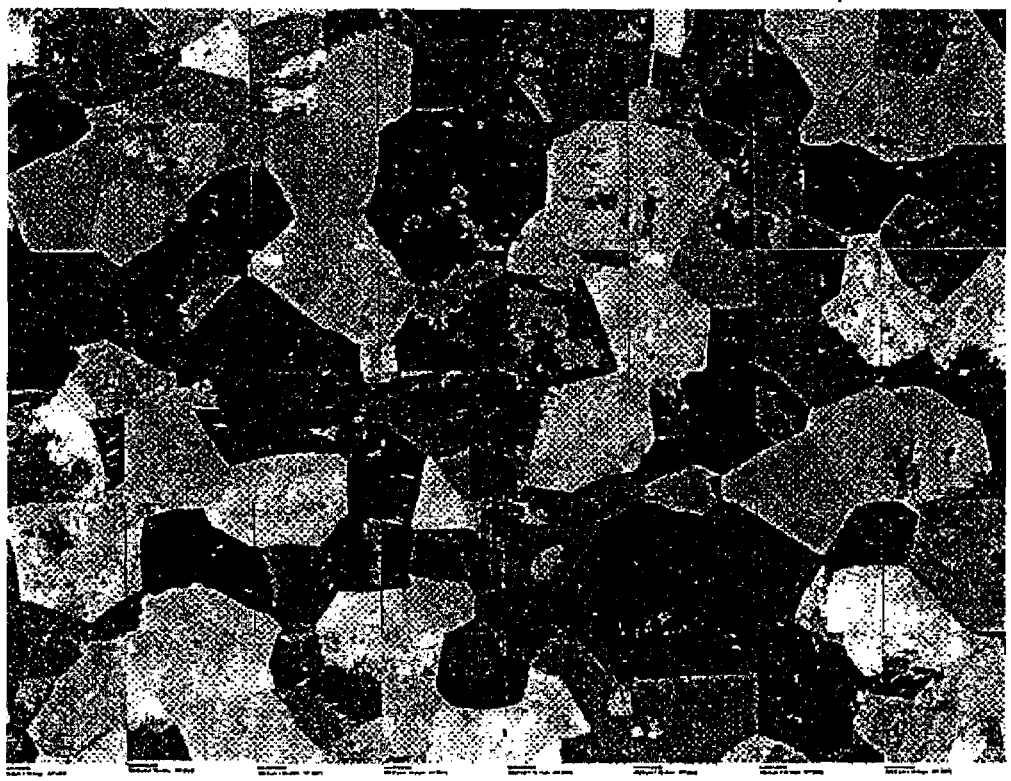
Beta  Fig. 3b

LAUE CRYSTALLOGRAPHIC ORIENTATION MAPPING SYSTEM

This application claims the benefit of provisional application 61/070,616 filed Feb. 15, 2008 under the provisions of 35 U.S.C. §119(e).

RIGHTS OF THE GOVERNMENT

The invention described herein may be manufactured and used by or for the Government of the United States for all governmental purposes without the payment of any royalty.

SUMMARY OF THE INVENTION

The invention relates to a device for measuring crystal orientation with an x-ray source using the Laue method and includes an apparatus for mapping a polycrystalline surface having a grain orientation. The apparatus including an x-ray source creating an x-ray beam, the beam having polychromatic photons, the beam collimated to a point on the polycrystalline surface. A two-dimensional x-ray detector with an aperture, the x-ray beam passing through the aperture, the detector detecting and collecting polychromatic photons diffracted from the polycrystalline surface and onto the detector. A means for moving the polycrystalline surface with respect to the x-ray source to collect a plurality of diffracted x-rays which define a Laue pattern. A data processing means to collect Laue patterns of the polycrystalline surface based on the plurality of diffracted x-rays, the Laue patterns identifying a plurality of crystallographic orientations and a plurality of grain surface areas on the polycrystalline surface.

BRIEF DESCRIPTION OF THE DRAWINGS

FIG. 3A is a black and white pictorial illustration of a titanium crystal structure before heating.

FIG. 3B is a black and white pictorial illustration of a heated titanium crystal structure.

DETAILED DESCRIPTION

The properties of many polycrystalline materials are strongly affected by their crystallographic orientation or texture. There are existing methods for the measurement of texture on a laboratory scale, but none are capable of being economically applied on a large scale. The manufacturing of components such as turbine disks and silicon wafers would greatly benefit from a method that could measure texture on a large scale. The Laue Crystallographic Orientation Mapping (LCOM) system is such a method.

Figure 1:
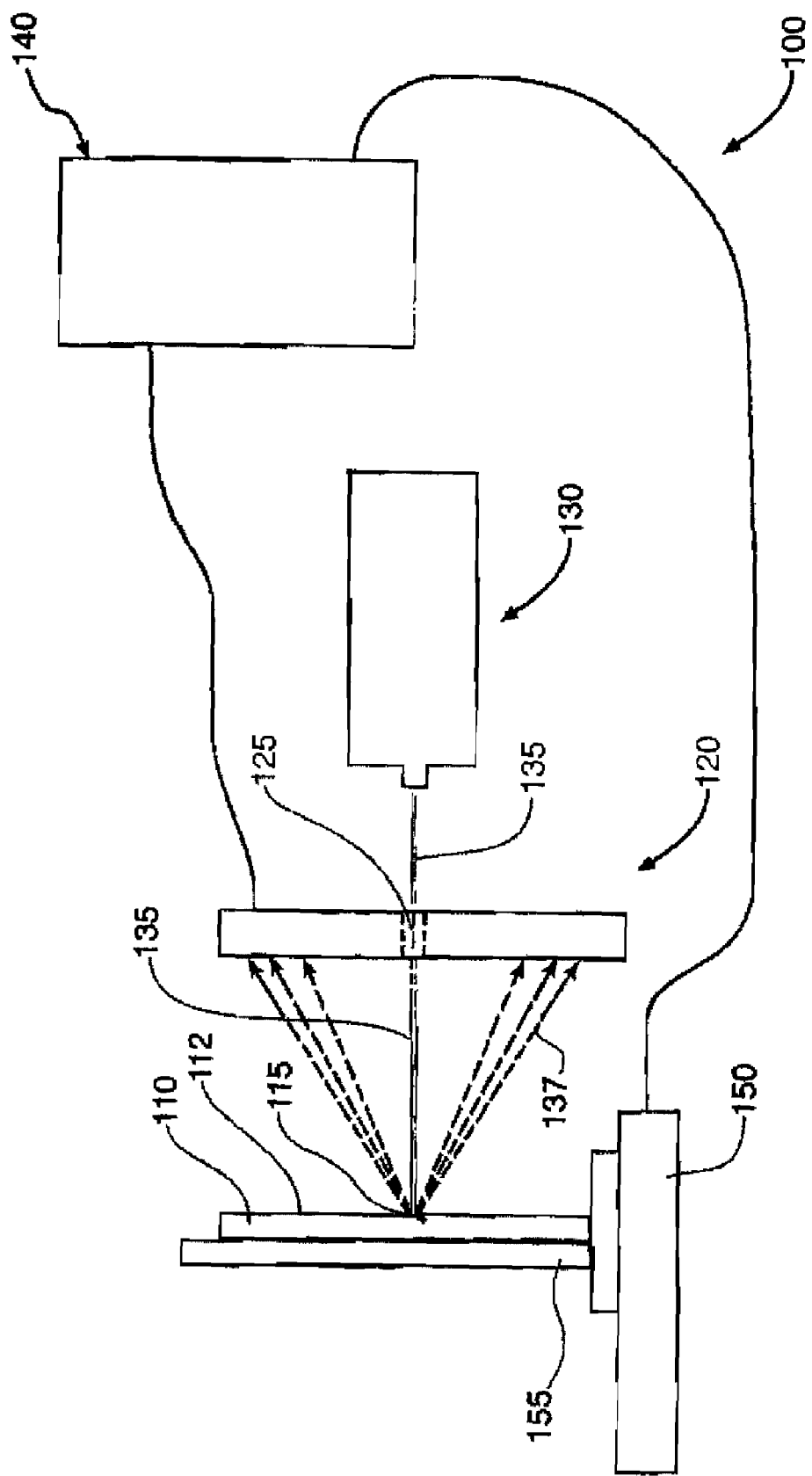
FIG. 1 is an illustration of one embodiment of the invention.

One embodiment of the LCOM apparatus is shown in FIG. 1. FIG. 1 includes an x-ray source 130 that produces an x-ray beam 135 that is collimated to a point 115 on a surface 112 of a polycrystalline specimen 110. Specific wavelengths of the polychromatic photons 137 emanating from the x-ray source 130 are diffracted by the specimen's grains or crystals and detected by a detector 120. Preferably the detector 120 has an aperture 125 through which the x-ray beam 135 may pass to impact the sample surface 112, but alternatively the detector 120 can also be mounted at an arbitrary angle to the specimen surface without the polychromatic photons 137 having to pass through the aperture 124 prior to impact with the surface 122 of the polycrystalline specimen 110. The detector detects and collects the diffracted polychromatic photons 137. The spatial locations where the diffraction criteria are satisfied form a unique signature known as a Laue pattern that characterizes the crystallographic orientation of the grain or crystal which diffracted the incident radiation. The LCOM system preferably uses a two-dimensional radiation detector to collect the Laue pattern and feed it to a data processing means 140, such as a computer.

A means for moving the sample 110 with respect to the detector 120 allows a plurality of diffracted polychromatic photons 137 to be detected and characterized as a function of the spatial location on the specimen surface 112. FIG. 1 shows a computer numerically controlled (CNC) system 150 with a movable base 155. At each spatial location on the specimen surface 112, the locations of the diffraction maximums which collectively form a Laue pattern are then computationally analyzed with the data processing means 140 to determine the crystallographic orientation of the grain/crystal being irradiated on the specimen surface 112. Once the irradiation, diffraction, and collection of the polychromatic photons are completed at one location on the specimen surface 112, the sample may be moved to characterize the crystallographic orientation of a grain/crystal at another location on the specimen surface 112. Alternatively, the x-ray source 130 and detector 120 may be moved with respect to the sample. Collectively the measured individual crystallographic orientations of the grains/crystals will form a spatial map of the crystallographic orientation of the individual grains/crystal as a function of their location along the specimen surface 112. The resolution of this map will depend on both the individual grain/crystal size in the polycrystalline specimen and the distance between adjacent locations whose Laue patterns were collected and analyzed. In one embodiment a Computer Numeric Control (CNC) system may be used to automatically move the specimen so that the process can be automatically repeated at the next location, but any other computerized means to translate the specimen can also be used.

An advantage to this system is that CNC G-codes may be used to efficiently provide a complete CNC mapping of the parts surface. G-codes are a common name for the programming language that controls CNC machine tools. Many CNC machines do not use G-codes, but rather some other proprietary system. The CNC integration with the computer may allow the use of any software communication known in the art for the surface of the part to be mapped and its crystal orientation determined. In one embodiment, the computer numeric control machine is controlled by the same software used to create a complex three-dimensional specimen surface 112. This may improve the precision of the sample measurements and/or reduce the cost of obtaining the crystal measurements on complex three-dimensional specimens.

In one embodiment, the apparatus includes a means to heat the crystal surface above ambient room temperature. The heating of the sample may be performed by any means known in the art. Possible methods on heating the sample include the use of resistive electrical heating, induction or radiant heat furnace designs in the ambient atmosphere. For specimens that will react chemically with the surrounding atmosphere at elevated temperatures, the region surrounding the specimen can be either filled with an inert gas or alternatively be evacuated. In one embodiment, the furnace/ambient environment barrier could be attached to the CNC gantry system and beryllium, kapton or amorphous quartz windows could be used to allow the polychromatic photons 135 emanating from the x-ray source 130 and the diffracted polychromatic photons 137 emanating from the specimen surface 112 to pass through with little attenuation. In one embodiment, the whole apparatus can be surrounded by an inert environment of place in under a vacuum.

In one embodiment, after having deduced the crystallographic orientation of a specific grain on the surface of a specimen, the locations of the Laue spot patterns and the shape of the spots produced will be used to calculate the strain and dislocation density present in the individual crystal (grain) being examined at one location. The successive Laue patterns generated during the mapping of a specimen surface will then be used to generate strain and dislocation density maps over the mapped surface.

In one embodiment, an energy dispersive spectrograph (EDS) is mounted to the apparatus at an oblique angle in order to collect the emitted spectrum from the surface of the specimen due to fluorescent scattering. This attachment will allow chemical mapping of the surface to be conducted simultaneously as a scan is being performed.

Preferably, the sample has a grain size of at least 50 µm, but grain sizes smaller than this could be accommodated with anticipated future improvements in the sensitivity of 2-D x-ray detectors. In this future embodiment, apertures would be used to reduce the footprint of the incident x-ray beam and hence allow specimens with smaller grain sizes to have the crystallographic orientation of the grains on the surface mapped. Grain sizes significantly larger than the footprint of the incident x-rays may be accommodated by adjusting the spacing between adjacent measurements on the surface of the specimen.

The apparatus disclosed above is one means of accomplishing a method of mapping a polycrystalline material. The method of mapping a polycrystalline surface may include applying x-rays to the surface such that a plurality of x-rays are diffracted off the polycrystalline surface at an angle. A plurality of the diffracted x-rays are detected and Laue patterns are generated based on the detected x-rays or diffracted polychromatic photons. The Laue patterns for a plurality of crystals on the polycrystalline surface are analyzed and mapped to determine the crystal size and orientation. The method preferably includes determining the Laue patterns at room temperature and/or at elevated temperatures in one embodiment.

The LCOM system collects data and operates in a fashion analogous to Orientation Imaging Microscopy (OIM), except that:

(1) LCOM does not require a Scanning Electron Microscope (SEM) with its costly and size limiting vacuum system. LCOM specimens are examined in open air.

(2) LCOM does not use an electron beam and resulting Kikuchi pattern maps to determine crystallographic orientation. LCOM uses an x-ray beam and its resulting Laue patterns.

(3) LCOM produces a map of the crystallographic orientation as a function of location over a large area by using a CNC driven gantry to move the specimen relative to the x-ray beam. Because there is no vacuum chamber involved, the area of this mapping is limited only by the CNC driven gantry system.

(4) LCOM allows the crystallographic orientation as a function of location on complex curved surfaces to be efficiently measured due to the use of CNC driven gantry devices to translate the specimen.

(5) LCOM allows the crystallographic strain in individual grains as a function of location to be deduced.

(6) LCOM allows the dislocation density on individual grains as a function of location to be deduced.

(7) LCOM does not require that the surface of the specimens be conductive, thus enabling non-conductive polycrystalline specimens to be examined without any additional surface preparation.

(8) LCOM does not require the same degree of surface preparation that OIM requires. For OIM, the surface of the specimen is polished to 0.15 µm or better finish (including electro-polishing in many cases), whereas Laue patterns using the LCOM methodology can be obtained in most materials on specimens prepared to 800 grit finishes.

A prototype system that operates in the manner described above has been designed and built. The prototype system uses a combination of commercially available components and in-house developed software. A standard CNC gantry by Techno Isel was used to translate the specimen in order to irradiate the various grains/crystals of the specimen with x-rays. The Laue patterns generated by the grains/crystals were collected on a two-dimensional x-ray detector produced by Multiwire. The coupling of the two systems was accomplished with custom software that allowed the two systems to operate in unison and produce single crystal data sets which can be analyzed by a Laue crystallographic software package developed by Daresbury Laboratories in the United Kingdom. The orientation of individual grains/crystals deduced by the Darebury software was then combined by another custom software package to produce maps of the crystallographic orientation as a function of location.

Due to the fact that the LCOM system uses x-rays instead of electrons, the size of the system is a function of the power of the x-ray source, the x-ray penetration depth of the various wavelengths used to generate the Laue pattern, the size and efficiency of the x-ray detector, and the size of the grains contained within the specimen. These factors interact with one another in a known fashion which will allow the size of the system to be scaled up or down to match the size of the specimens to be examined. Thus, a desktop version could be constructed for smaller specimens such as metallurgical mounts. For larger specimens, very large CNC gantry systems capable of supporting and translating large specimens could be designed. For complex surfaces, the coupling of CNC technology will enable other CNC standard machining fixtures (e.g., an A-stage) to be combined with an XYZ gantry system to follow complex surfaces with standard G-code CNC programs.

Because the method uses x-rays, the LCOM technique can be used to map conductive as well as non-conductive materials. Therefore, it can be used to map the texture in large forgings, silicon wafers and ceramic castings. Examples of applications include: non-destructively find defects (freckles) in directionally solidified turbine blades; serve as a Quality Assurance tool in the manufacturing of sputtering targets used in the electronics industry; and measure the texture on-line of superconducting tapes. It could also be coupled with other emerging technologies such as the serial microstructure imaging efforts being developed to produce a three-dimensional data set that describes microstructure and crystallographic orientation on large grain specimens. In general, the application of this technology is dependent on the speed and efficiency of the detectors and computers used in the systems developed. The present invention is capable of mapping grain structures down to about 50 µm. The present invention, with the current x-ray detection system, may map the grain structures at a speed of about 0.25 Laue images per second.

Figure 2B:
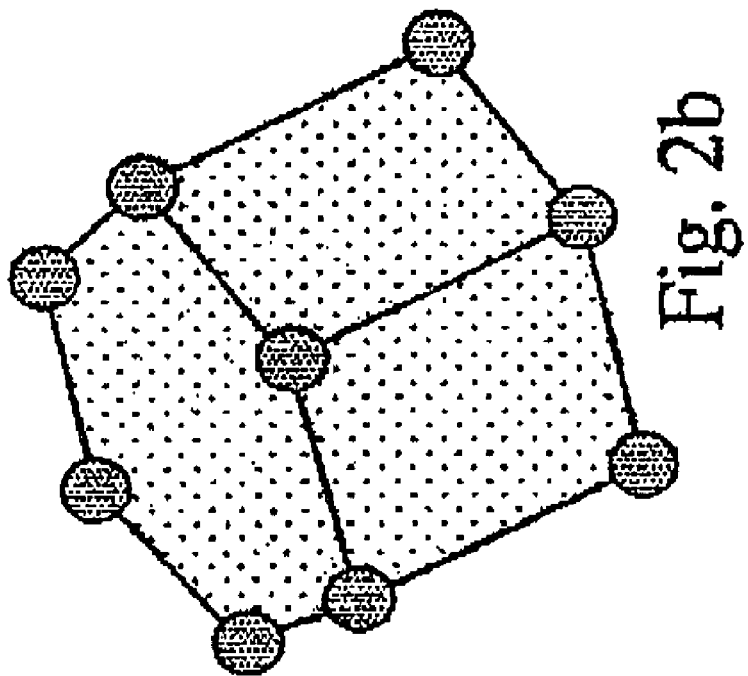
FIG. 2B is an illustration of a heated titanium crystal structure.
Figure 2A:
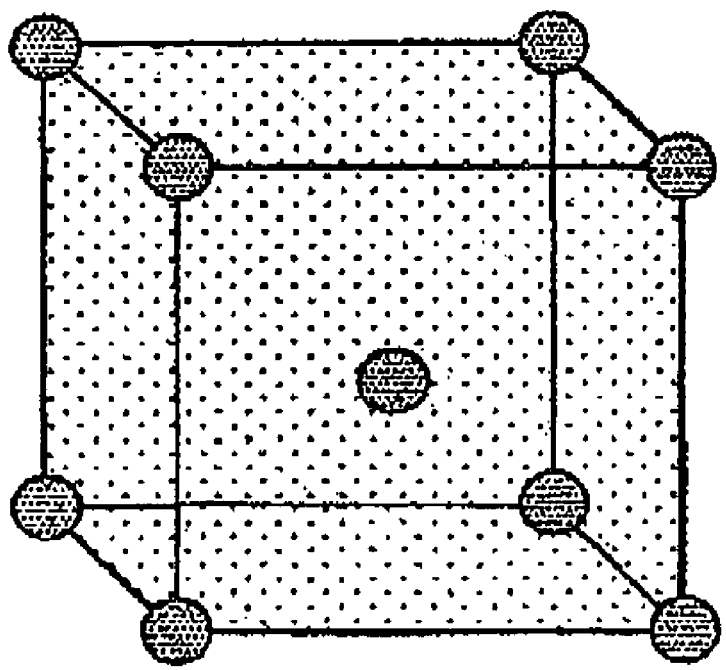
FIG. 2A is an illustration of a titanium crystal structure before heating.

In one embodiment the sample is heated above 500° C. and then mapped. In one embodiment the sample heated is above 550° C. and then mapped. For samples containing titanium, the sample may be heated to more than 850° C. Prior to heating, the material is in the Alpha phase as shown in FIG. 2A. This phase may be hexagonal close packed and have few slip systems. Once heated, the sample typically has a Beta phase shown in FIG. 2B. The Beta phase may be Body Centered Cubic (BCC) and has many more slip systems as compared to the Alpha phase. Mapping and the Beta phase may provide better information under crystallographic structure of the sample. Computer software defines the crystal orientation for $(\phi_1, \phi, \phi_2) = (0, 0, 0)$ in the HCP structure. The data processing means program them reduces the Euler space populated with EBSD data for each alpha variant by using the symmetry of the hexagonal crystal structure to eliminate redundancy. These calculations are then analyzed to determine the minimum number of distinct ways in which and orientation of the Hexagonal Close Packed (HCP) phase can be transformed into a single Body Centered Cubic (BCC) phase orientation. A minimization of mis-orientation approach is used to determine an approximate best fit solution for the parent-phase orientation.

This process may be automated for efficient calculations. A unique identification number (GID) for the sets of Euler angles from each alpha-phase variant is used to identify those phases adjacent to each other. The adjacent alpha variants may be identified using a Monte-Carlo simulation.

A pictorial example of the above phase shift is shown in FIGS. 3A and 3B. FIG. 3A shows the alpha phase while FIG. 3B shows that beta phase.

While specific embodiments have been described in detail in the foregoing description and illustrated in the drawings, those with ordinary skill in the art may appreciate that various modifications to the details provided could be developed in light of the overall teachings of the disclosure.

What is claimed is:

1. An apparatus for mapping a specimen having a grain orientation, the apparatus including in combination:
    the specimen having a polycrystalline surface;
    an x-ray source creating an x-ray beam, the beam having polychromatic photons, the beam collimated to a point on the polycrystalline surface;
    a two-dimensional x-ray detector with an aperture, the x-ray beam passing through the aperture, the two-dimensional x-ray detector detecting and collecting a plurality of polychromatic photons diffracted from the polycrystalline surface and on to the two-dimensional x-ray detector which define a Laue pattern;
    a Computer Numeric Control (CNC) system for moving the specimen with respect to the x-ray source and the two-dimensional x-ray detector;
    a data processing means to direct the Computer Numeric Control (CNC) system to move the specimen and to collect Laue patterns as a function of the spatial location on the polycrystalline surface to the two-dimensional detector; and
    the data processing means further identifying a plurality of crystallographic orientations and a plurality of grain surface areas on the polycrystalline surface based on the Laue patterns.

2. The apparatus of claim 1 wherein the polycrystalline surface is heated to at least 500° C. while detecting the Laue patterns.

3. The apparatus of claim 1 wherein the two-dimensional x-ray detector can detect a grain size of at least 50 μm or more on the polycrystalline surface.

4. The apparatus of claim 1 wherein a region surrounding the specimen is filled with an inert gas.

5. The apparatus of claim 1 wherein a region surrounding the specimen is evacuated.

6. The apparatus of claim 1 wherein the apparatus calculates the strain and dislocation density present from the Laue patterns.

7. The apparatus of claim 1 wherein an energy dispersive spectrograph (EDS) is mounted to the apparatus at an oblique angle to simultaneously chemically map the polycrystalline surface.

8. The method of claim 1 wherein the polycrystalline surface is mapped both before and after being heated.

9. The apparatus of claim 8 wherein successive Laue patterns generate a mapping of the polycrystalline surface prior to being heated and after being heated, the map therein used by the data processing means to calculate strain and dislocation density maps over the mapped polycrystalline surface.

* * * * *